United States Patent [19]

Wong et al.

[11] Patent Number: 5,308,625
[45] Date of Patent: May 3, 1994

[54] ENHANCEMENT OF TRANSDERMAL DRUG DELIVERY USING MONOALKYL PHOSPHATES AND OTHER ABSORPTION PROMOTERS

[75] Inventors: Ooi Wong, Fremont; Thuytien N. Nguyen, Hayward, both of Calif.

[73] Assignee: Cygnus Therapeutic Systems, Redwood City, Calif.

[21] Appl. No.: 938,775

[22] Filed: Sep. 2, 1992

[51] Int. Cl.[5] ............................................. A61F 13/00
[52] U.S. Cl. ................................. 424/449; 514/946; 514/947
[58] Field of Search ................. 424/447, 449; 514/946, 514/497

[56] References Cited

U.S. PATENT DOCUMENTS 5,091,186  2/1992  Miranda et al. ...................... 424/448

OTHER PUBLICATIONS

Takeshita e al., *Circulation*, 55:401 (1977).
Noack et al., *Pharmacology*, 14(11):S1-S5 (1989).
Ostrowski et al., *Amer. Heart Journal*, pp. 641-643, (1985).
Kulovetz et al., *Amer. Heart Journal*, pp. 637-640 (1985).
Schmutzler, *Amer. Heart Journal*, 109:723-724 (1985).

*Primary Examiner*—Thurman K. Page
*Assistant Examiner*—Jyothsna Venkat
*Attorney, Agent, or Firm*—Morrison & Foerster

[57] ABSTRACT

Pharmaceutical formulations, transdermal drug delivery devices, and methods of drug delivery using the formulations and devices of the invention are disclosed which make it possible to enhance the rate of transdermal drug delivery of pharmaceutically active compounds and in particular molsidomine. The rate of drug delivery is increased by using absorption promoters which include monoalkyl phosphates and salts thereof alone or in combination with other absorption promoters such as polyhydroxyl esters, longchain fatty acids, polyhydroxyl alcohols and terpenes. Particular combinations of monoalkyl phosphates with one or more additional absorption promoters provides synergistic effects with respect to enhancing the rate of drug delivery of certain pharmaceutically active drugs such as molsidomine.

14 Claims, 8 Drawing Sheets

ENHANCEMENT OF TRANSDERMAL DRUG DELIVERY USING MONOALKYL PHOSPHATES AND OTHER ABSORPTION PROMOTERS

FIELD OF THE INVENTION

This invention relates generally to the field of compounds used as permeation enhancers for enhancing the rate of transdermal drug delivery. More specifically, the invention relates to monoalkyl phosphates which, when used alone and/or in combination with other absorption promoters, greatly enhance the transdermal delivery of pharmaceutically active drugs such as molsidomine.

BACKGROUND OF THE INVENTION

For sometime it has been known that it is possible to administer drugs to a patient by transdermal drug delivery systems. Essentially, the methodology involves placing the drug on the surface of the skin and/or mucous membrane and allowing the drug to permeate through the skin into the patient's blood supply for systemic relief and/or to the specific location where relief is required in order to obtain a local effect. Transdermal drug delivery works well for some drugs and not so well for others which are not readily absorbed through the skin. When a drug is not readily absorbed through the skin, other methodologies and/or compounds can be used in order to enhance the rate of absorption, i.e., get more drug through the skin in a given unit of time.

One well-known method of enhancing the rate of drug delivery is to add an additional component which acts as an absorption promoter, i.e., a compound which enhances the rate of transdermal drug permeation through the skin. Different permeation enhancers operate by different mechanisms. Further, drugs which do not absorb well through the skin are hindered for different reasons. Accordingly, not all permeation enhancers will enhance the permeation of all drugs. The permeation enhancer must be characterized by assisting in overcoming a difficulty which causes the particular drug not to be absorbed well. One drug which is known not to be absorbed well through the skin is molsidomine.

Molsidomine (N-5-ethoxycarbonyl-3-morpholinosydnonimine) is a novel sydnonimine derivative with a mesoionic aromatic ring. It is also an ester prodrug.

Molsidomine is a white colorless crystal powder, practically tasteless or odorless. The imine has a molecular weight of 242 with a melting point of 140°–141° C. and a $pK_a$ value of 3.34 at 25° C. Its maximum UV absorption wavelength is 326 nm in $CHCl_3$. The solubilities of molsidomine in various solvent systems are shown in Table I.

TABLE I

| | Saturated Solubilities of Molsidomine in Various Vehicles | |
|---|---|---|
| | Vehicles | Solubilities at 25° C. (%) |
| 1 | Glycol salicylate | 15.1 |
| 2 | Propylene glycol | 6.37 |
| 3 | PEG 400 | 5.23 |
| 4 | Glycerin | 1.80 |
| 5 | Oleic Acid | 1.37 |
| 6 | Octyl.decyl oil | 0.36 |
| 7 | Isopropyl myristate | 0.09 |

Reference: Yamada et al., Chem. Pharm. Bull., 35, 3399–3406 (1987).
*Freely soluble in $CHCl_3$
*Soluble in dil HCl, ethanol, ethyl acetate and methanol
*sparingly soluble in water, acetone, benzene
*very slightly soluble in ether, petr ether
Reference: Merck Index, 10$^{th}$ edition, page 892 (1983)

It is soluble in propylene glycol and a variety of organic solvents. The chemical stability of molsidomine has been investigated in detail by Asahi et al. (1971). It is most stable in aqueous solution of pH 5 to 7 (Table II), but is photosensitive, particularly in sunlight.

TABLE II

| Chemical Stability of Molsidomine | |
|---|---|
| pH | $t_{90}$ (days) at 20° C. |
| 1–2 | 38 |
| 4 | 250 |
| 5–7 | 950 (2.6 years) |
| 10 | 400 |
| 11 | 40 |

Reference: Yutaka Asahi, K. Shinozaki, and M. Nagaoka, Chemical & Pharmaceutical Bulletin, Vol 19, 1079–1088 (1971)

Molsidomine has been shown to possess a sustained anti-anginal effect and can be metabolized to SIN-1, which is readily converted into the active metabolite SIN-1A (carries a free nitroso group), Scheme 1.

A very recent investigation on the vasodilation action of molsidomine and other vasodilators, including nitroglycerine reveals that it is the nitric oxide, liberated from the active metabolite SIN-1A, that activates the soluble guanylate cyclase, which in turn causes vasodilation. This is a major difference from the vasodilation action of nitroglycerin.

The coronary vasodilation action of nitroglycerin depends on the presence of cysteine. Cysteine deficiency was found to be associated with tolerance developed for nitroglycerin uses. After prolonged exposure to nitroglycerin, tolerance toward the drug developed in coronary strips can be antagonized by cysteine. However, the active metabolite of molsidomine, SIN-1A, is active in both the presence and absence of cysteine; therefore, molsidomine produces insignificant tolerance (Kulovetz and Holzmann, 1985) making it a better alternative for anti-anginal therapy.

Transdermal delivery of molsidomine has been studied and it has been shown that in an in vivo rat experiment a combination of propylene glycol with 10% oleic acid produced an estimated flux of 399 $\mu$g/hr-cm$^2$ for molsidomine.

It has also been shown that a single oral dose of 2 mg of molsidomine can produce anti-anginal effects in patients with coronary heart disease for 3 to 5 hours. Different oral dosing levels can benefit patients with different degrees of coronary heart disease. Typically, it is suggested that oral doses of 2 mg three times daily, or 4 mg four times daily should be given. Pharmacokinetic data indicate that the total clearance and peak plasma concentration of molsidomine were 46,000 ml/hr and 15 mg/ml, respectively, following the administration of an oral dose of 2 mg. The bioavailability of molsidomine from oral doses is 44%. Generally, the effective blood concentration of a drug is less than the peak plasma concentration; therefore, an estimation of target flux based on the effective blood concentration should be a better indication of the delivery rate required to produce therapeutic response.

European patent application 0,127,468, entitled "Percutaneous Pharmaceutical Preparation for External Use," was published Dec. 6, 1984. The application discloses pharmaceutical percutaneous formulations containing various amounts of molsidomine and various absorption promoters.

SUMMARY OF THE INVENTION

Transdermal drug delivery devices, pharmaceutical formulations and methods of enhancing the transdermal delivery of pharmaceutically active drugs are disclosed. The invention is particularly directed to such devices, formulations and methods which enhance the transdermal administration of molsidomine using one or more permeation enhancers selected from the group consisting of monoalkyl phosphates and salts thereof combined with one or more of (1) a polyhydroxyl ester; (2) a long chain fatty acid; (3) a polyhydroxyl alcohol; and (4) a terpene.

An important object of the present invention is to provide a transdermal drug delivery device which includes an absorption enhancer in the form of a monoalkyl phosphate and/or salts thereof, alone or in combination with other absorption promoters which promote the absorption of a pharmaceutically active drug and, in particular, the absorption of molsidomine.

Another object of the invention is to provide pharmaceutical formulations comprised of absorption promoters which include monoalkyl phosphates and salts thereof, alone or in combination with other absorption promoters, and a pharmaceutically active drug which is preferably molsidomine.

Another object of the present invention is to provide methods of enhancing the absorption of pharmaceutically active drugs and, in particular, methods of enhancing the absorption of molsidomine using absorption promoters which include monoalkyl phosphates and salts thereof.

An advantage of the present invention is that the rate of absorption of pharmaceutically active drugs and, in particular, molsidomine is greatly increased.

A feature of the present invention is that the transdermal devices and pharmaceutical formulations can be readily formulated utilizing the nontoxic, biocompatible absorption promoter compounds of the invention.

These and other objects, advantages and features of the present invention will become apparent to those persons skilled in the art upon reading the details of the formulation and usage as more fully set forth below, reference being made to the accompanying examples forming a part hereof.

DETAILED DESCRIPTION OF THE INVENTION

Before the present transdermal drug delivery devices, formulations and methods of drug delivery are described, it is to be understood that this invention is not limited to the particular devices, formulations or methods described as such may, of course, vary. It is also to be understood that the terminology used herein is for the purpose of describing particular embodiments only, and is not intended to be limiting since the scope of the present invention will be limited only by the appended claims.

It must be noted that, as used in this specification and the appended claims, the singular forms "a," "and," and "the" include plural referents unless the context clearly dictates otherwise. Thus, for example, a reference to "a monoalkyl phosphate" includes mixtures of such compounds, reference to "an enhancer" includes mixtures of enhancers of the same general type described herein and reference to "the excipient carrier" includes mixtures of, and related types of, excipient carriers generally used by those skilled in the art and so forth.

Unless defined otherwise, all technical and scientific terms used herein have the same meaning as commonly understood by one of ordinary skill in the art to which this invention belongs. Although any methods and materials similar or equivalent to those described herein can be used in the practice for testing of the present invention, the preferred materials and methods are described herein. All publications mentioned herein are incorporated herein by reference in their entirety.

A number of abbreviations standard in this field are used throughout the application and attached figures as follows: $CHCl_3$ for chloroform; PEG for polyethylene glycol; HCl for hydrochloric acid; $\mu$l for microliter; $\mu$g for microgram; HPLC for high-performance liquid chromatography; $NaH_2PO_4$ for monosodium phosphate; min. for minute; PGML for propylene glycol monolaurate; PG for propylene glycol; $DDPO_4$ for mono-dodecyl phosphate; MOSD for molsidomine; $CH_3OH$ for methanol; $H_2O$ for water; OA for oleic acid; LA for lauryl alcohol.

In order to describe how to make and use the invention, it is most logical to first describe how to make the pharmaceutical formulations of the present invention in that these formulations can be used in making the transdermal drug delivery devices and both the formulations and the devices can be used in carrying out the methods of the invention. The essence of the invention can be understood without reference to the specific examples. However, the examples are provided in order to demonstrate the effectiveness of the claimed invention in enhancing transdermal drug delivery by greatly increasing the rate of drug delivery across the skin. Further, the examples demonstrate the synergistic effect obtained by the use of different combinations of absorption promoters.

PHARMACEUTICAL FORMULATIONS

In essence, pharmaceutical formulations of the invention include two components which are (1) a pharmaceutically active drug and (2) an absorption promoter. However, the formulations will, in most circumstances, include an additional component (3) in the form of pharmaceutically acceptable excipient carrier.

The pharmaceutically active drug is most preferably molsidomine. Other drugs can be combined with molsidomine in the formulation or substituted for molsidomine. However, if molsidomine is not present, then the pharmaceutically active drug will have a number of characteristics related to molsidomine which allow the drug to be acted upon in the same manner with respect to the absorption promoters and thereby enjoy the benefits of the absorption promoters to substantially the same degree as molsidomine.

The absorption promoter will include a monoalkyl phosphate and/or a salt thereof. A range of different monoalkyl phosphates and salts are disclosed and any one can be used alone or in combination with others in different proportional amounts without affecting the results obtained by the present invention. The main absorption enhancer, which is the monoalkyl phosphate or salt thereof, can be used alone or in combination with one or more additional absorption enhancers which are present within four distinct groups as follows: (1) polyhydroxyl esters; (2) longchain fatty acids; (3) polyhydroxyl alcohols; and (4) terpenes. The additional absorption promoters may be present individually or in any combination of (1)-(4) and each preferably contains about 8 to 30 carbon atoms. The additional absorption promoter may be present in any given amount but is preferably present in an amount substantially greater than the amount by weight of the monoalkyl phosphate absorption promoter, e.g., 2 to 20 times as much.

Pharmaceutical formulations of the present invention preferably include molsidomine (MOSD) as the pharmaceutically active drug. Such formulation preferably comprise about 1-15% MOSD and about 99-85% absorption enhancer (by weight) which is preferably all $DDPO_4$ or a salt thereof. The absorption enhancer such as $DDPO_4$ may be present in a matrix or other carrier and present in a ratio of 1:99 to 20:80 of $DDPO_4$: matrix and/or vehicle. A particularly preferred formulation includes about 5% MOSD, 10% $DDPO_4$ and 85% PGML. A particularly preferred matrix will include about 6% MOSD, 6% PGML and 88% matrix which is most preferably silicone 2920. All ratios and % amounts are by weight.

The pharmaceutically active drug can be combined with the absorption promoter to form the formulation. However, in order to provide for commercially useful formulations, it is generally desirable to include pharmaceutically acceptable excipient materials which can include water, alcohols and, in particular, lower-chain alcohols such as isopropyl alcohol, various aqueous solutions such as saline solutions, and sucrose solutions, and other liquid excipients known to those skilled in the art, which excipients can be readily determined to mix well with the absorption promoters and pharmaceutically active drugs used in connection with the present invention.

As indicated above, an essential feature of the invention is that it includes a monoalkyl phosphate or salt thereof as an absorption promoter. A range of different monoalkyl phosphates, salts and mixtures of each and/or both can be used. In general, monoalkyl phosphates have the following general structural formula:

wherein "n" is in the range of from about 7 to about 29. In one preferred embodiment n is 11, thus providing the following monoalkyl phosphate:

The above structure shows the structure of monododecyl phosphate also referred to as phosphoric acid mono-dodecyl ester which has a melting point in the range of about 58° C. to about 63° C. and a molecular weight of 266. Other monoalkyl phosphates can be used and the alkyl moiety will generally contain 8 to 30 carbon atoms. Any pharmaceutically useful salts of the monoalkyl phosphates can also be used such as sodium and potassium salts.

The monoalkyl phosphates and salts thereof as used in combination with other absorption promoters greatly enhance the transdermal drug delivery rate of pharmaceutically active drugs through biological membranes including the skin, nasal membranes, buccal membranes, rectal membranes, gastric, intestinal and vaginal membranes. Accordingly, the pharmaceutical formulations of the present invention can be placed on any of these membranes in order to enhance the drug delivery rate of drugs through the membrane and into the patient being treated.

In addition to the absorption promoter, the pharmaceutical preparation according to this invention can be compounded with a base component, any alcohol such as benzylalcohol, propylene glycol, sorbitol solution, glycerin, polyethylene glycol, etc., vegetable oils and fats such as olive oil, safflower oil, cottonseed oil, etc., animal oils and fats such as squalene, squalene, lanolin, etc., paraffins such as liquid paraffin, vaseline, etc., higher fatty acid esters such as isopropyl myristate, isopropyl palmitate, diethyl sebacate, glycerin esters such as monoacetin, diacetin, capryltriglyceride, caprintriglyceride, etc., and/or ethyl cellosolve, methyl cellosolve, etc., in suitable proportions, although the preferred proportion of such base component is generally 10 to 95% by weight.

In addition to the absorption promoter and base component mentioned above, the pharmaceutical preparation for percutaneous absorption according to this invention may contain a component for controlling the percutaneous absorption of molsidomine to thereby ensure a sustained blood concentration, such as solid paraffin, beeswax, carnauba wax, hydrogenated castor oil, lanolin, polyethylene glycol (e.g., PEG 400, 1500, 4000), spermwax, glyceryl monostearate, cholesterol, carbopol, carboxymethylcellulose, carboxyethylcellulose, silicone resin, etc., in suitable proportions, although the preferred proportion of such controlling component is generally 10 to 95% by weight.

In accordance with this invention, a pharmaceutical composition for percutaneous absorption containing the aforementioned components can be applied to any human body surface, either as it is or as formulated into any of the hydrophilic, oleaginous and emulsion forms mentioned in the Japanese Pharmacopeia and/or Remington's Pharmaceutical Sciences, Mack Publishing Co., Easton, Pa. (latest edition) incorporated herein by reference.

A particularly preferred formulation contains about 5% molsidomine, 10% monododecyl phosphate and 85% propylene glycol monolaurate.

TRANSDERMAL DRUG DELIVERY DEVICES

In essence, the transdermal drug delivery devices of the invention include a support base which is preferably a flexible, substantially planer support material having a pharmaceutically active drug (preferably molsidomine) and an absorption enhancer which includes a monoalkyl phosphate or salt thereof thereon.

The support base may be comprised of a variety of different types of materials. For example, the support base may be comprised of a substantially planer and flexible material which conforms to the shape of the human body when applied to the skin. Such materials may be high molecular weight polymer film such as polyethylene, polypropylene, polyvinyl chloride, polyethylene terephthalate, polytetrafluoro-ethylene, cellulose acetate, cellulose nitrate, polyacrylonitrile, ethylene-vinylalcohol copolymer and polydimethylsiloxane, woven fabric, non-woven fabric composed of, for example, nylon, polyester, polypropylene and polyethylene, paper and so on. The support material is preferably porous such that it has a moisture vapor transmission rate compatible with human skin. Silicone materials are particularly preferred as an absorption matrix into which the drug and absorption promoter are absorbed. Other materials compatible with the skin and capable of absorbing the formulation and releasing it to the skin can also be used.

When the invention is made available in the form of an adhesive tape, sheet or patch, the adhesive agent may be selected from among materials of polyalkylvinylether, polyalkyl acrylate, polyisobutylene, natural rubber, synthetic rubber and so on. Further, for the purpose of importing suitable degrees of plasticity and adhesivity, it is possible to add animal or vegetable oil, vaseline, lanolin or the like, or/and, as an antieruption component, an antihistaminic agent such as diphenhydramine, etc.

In most clinical studies of molsidomine, daily oral dosing of 2 mg for 3 to 4 times has been shown to be effective for the treatment and prevention of anginal pectoris. The total daily dose will be 6 to 8 mg. However, the absolute bioavailability of the molsidomine from oral administration is 44% indicating only 2.64 to 3.52 mg is required to be delivered transdermally; therefore, the target flux for a 20 cm$^2$ molsidomine transdermal therapeutic system is estimated to be about 5.5 to 7.5 $\mu$g/hr-cm$^2$.

A particularly preferred device is comprised of about 6% molsidomine, about 6% absorption promoter, and about 88% matrix which is silicone, e.g., silicone 2920. The absorption promoter is most preferably monododecyl phosphate and propylene glycol monolaurate.

METHODS OF USE

In essence, the methods of the present invention involve applying a therapeutically effective amount of the pharmaceutical formulation and/or a transdermal drug delivery device which includes a therapeutically effective amount of the pharmaceutical formulation to the skin and/or mucous membrane of a patient and allowing the formulation or device to remain in place for a sufficient amount of time to deliver a therapeutically amount of a drug to the patient. To obtain a therapeutical effect, the drug must be delivered in sufficient amount at a rate such that a desired effect is obtained. The effect to be obtained, of course, varies depending on the particular drug being delivered. With respect to molsidomine, the effect to be obtained is a vasodilator effect which, if sufficient, relieves angina and/or prevents its occurrence. Accordingly, the effect obtained is systemic. In some instances, the drug being delivered will provide only a local effect. It is most desirable to devise the transdermal drug delivery device so that it can be applied once a day by the patient. This is done in order to maximize patient compliance with an easy-to-follow dosing protocol. In certain circumstances, the pharmaceutical formulation can be applied directly to the skin or mucous membrane by itself or applied and then covered with a conventional bandage.

EXAMPLES

The following examples are put forth so as to provide those of ordinary skill in the art with a complete disclosure and description of how to make and use the formulations and drug delivery devices of the invention and demonstrate the operability of such and are not intended to limit the scope of what the inventors regard as their invention. Efforts have been made to ensure accuracy with respect to numbers used (e.g., amounts, temperature, etc.) but some experimental errors and deviation should be accounted for. Unless indicated otherwise, parts are parts by weight, molecular weight is average molecular weight, temperature is in degrees Centigrade, and pressure is at or near atmospheric.

The various materials, methodologies, and formulation components used in connection with the invention are first described in detail followed by a description of various testing procedures.

Materials

Molsidomine was obtained from Sigma. Propylene glycol monolaurate (PGML), used in the skin permeation studies, was obtained from Gattefosse (Elmsford, N.Y.). Morstik 607 was obtained from Morton-Thiokol, Silicone 2920 from Dow Corning, and Gelva 2333 from Monsanto. Mono-dodecyl phosphate ester was obtained from Lancaster, N.H.

Analytical Methods

The concentration of molsidomine in the samples was analyzed by HPLC analytical methods. The HPLC apparatus includes a Perkin-Elmer Diode array detector LC-235, a Perkin-Elmer automatic samples ISS 100C, a Perkin-Elmer pump, and a Quarternary LC pump 620. A column, 100×4.6 mm (ID), packed with Spheri-5-RP-18 (OD-MP) (5 microns) equipped with a guard column, 15×3.2 mm (ID, packed with RP-18, 7 microns) used in the separation was obtained from Applied Biosystems. Several HPLC running conditions have been developed.
  A. The mobile phase was 0.025 M $NaH_2PO_4$ (82%): acetonitrile (18%) with a flow rate of 1.0 ml/min, detection wavelength of 315 nm, and retention time of 3.0 min.
  B. The mobile phase was methanol (40%) and water (60%) with a flow rate of 1.0 ml/min, detection wavelength of 315 nm and retention time of 2.8 min.

Figure 1:
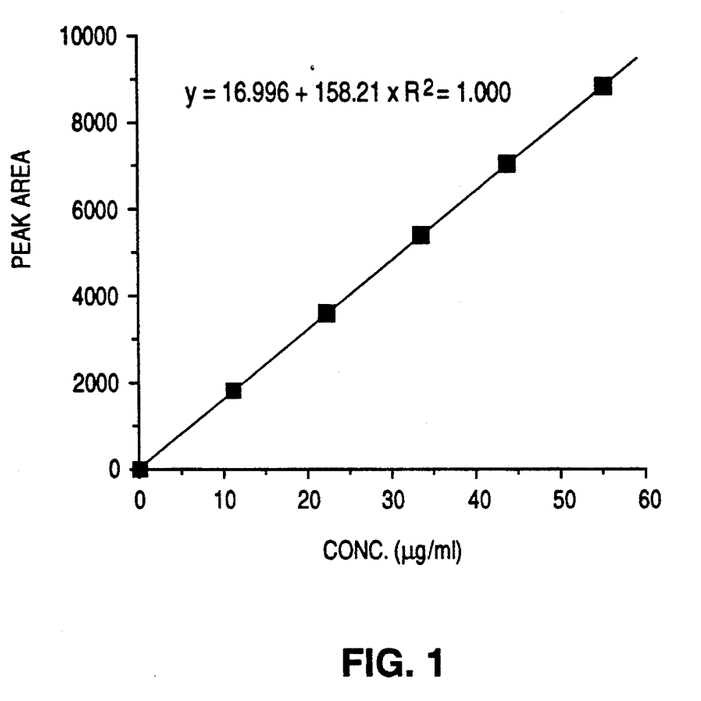
FIG. 1 is a graph showing a standard HPLC chromatogram for molsidomine.

Method (B) has some advantages over that of (A) in that a less expensive solvent, methanol, is used in place of the more expensive acetonitrile, and no phosphate is necessary, which can prolong the column working life. A range of 1 to 55 μg/ml showed linearity in the standard curve. FIG. 1 shows an HPLC chromatogram and a standard curve of molsidomine. For skin flux samples showing high concentration, off-column dilution of the samples is necessary to interpret the concentrations from the standard curves. Molsidomine has been reported to be photosensitive and therefore all the molsidomine solutions were stored in amber vessels.

Solubilities in Vehicles

Molsidomine powder was weighed on weighing paper and transferred into the sample vial. Solvent was transferred into the vial followed by insertion of a small Teflon-coated magnetic stirring bar. The sample vial was screw-capped and placed on top of a multiple stirring system obtained from Florida Scientific, Inc. and housed in an incubation oven at 32° C. The sample solutions were examined for saturation. More molsidomine was added to the solutions until saturation was achieved.

The saturated solutions were filtered through a micro filter to remove excess solid molsidomine. The filtered samples were then assayed for molsidomine concentration by the HPLC analytical method.

Preparation of Solution Formulations

Generally, one or two ml of a saturated solution made with a single vehicle or combination of vehicles were prepared for the skin flux experiments. The combination vehicles were first prepared in an amber vial by mixing the proportion of vehicles, and then a small portion of molsidomine powder in the range of 20 to 50 mg was added to the vehicles. The mixtures were stirred with a small magnetic bar and more molsidomine powder was added to the vials as the solid dissolved. In this way, the solubility of molsidomine in the particular vehicle(s) was estimated.

Fabrication of Monolithic Matrices

Each formulation was mixed with a rotatory mixer for at least 1-2 hours until it formed a homogeneous solution or suspension. The mixture was incorporated with various amounts of molsidomine and vehicles. The material was spread evenly on a polyethlyene plastic sheet to make a film with various thickness of 10-40 mils (wet) by a Gardner knife. The film was allowed to dry in a hood for at least 20 minutes and then further dried in an oven at 70° C. After cooling the cured films, a release liner was used to cover the films and they were stored in plastic bags until use.

Basically, the matrix monolithics is a drugcontaining matrix layer having a release liner coating on each surface. The release liner is removed from one surface to expose a surface of drug matrix which is applied to the surface of the skin.

EXAMPLE 1

Skin Flux Experiments

Human cadaver epidermis was removed carefully from dermatomed full thickness skin after the skin had been heated in deionized water at 60° C. for one to two minutes. The stripped epidermis was placed between two polyethylene plastic sheets and kept in a refrigerator until use. Discs of the epidermis with diameter of ⅝ inch were punched out with a die and tested for leakage. This was done by first soaking the epidermis in water and then spreading it flat on a plastic sheet, followed by pressing a piece of laboratory tissue on top of the epidermis a few times. Leakages of the epidermis showed wet spots on the tissue.

An epidermis disc was placed on top of the receiver cell of a modified Franz vertical diffusion cell assembly followed by placing the donor cell on top of the receiver cell. A small magnetic stir bar was inserted through the sampling port into the receiver cell compartment. The diffusion cell assemblies were clamped together and transferred to a thermostatted room (32° C). The receiver cell compartments were filled with 8.0 ml of the isotonic phosphate buffer of pH 5.0. An isotonic phosphate buffer of 7.0 was also used for skin flux comparison. For solution formulations, 0.2 ml of a particular liquid formulation was applied to the donor cell compartments which were then sealed by a Teflon plug. As for matrix formulations, an appropriate size of the matrix discs (diameter of ⅝ inch) were punched with a die. The release liner was removed and the matrix placed onto the epidermis before clamping the diffusion cell assembly together. The weights of the matrix were calculated from the difference in weight between the two release liner discs and the matrix discs. The amount of molsidomine in the donor cell was then calculated.

At the appropriate sampling time point, 1.0 ml of sample was replaced by 1.0 ml of fresh buffer.

Skin Flux Data Manipulation

The amount of molsidomine in each sample was assayed by the HPLC analytical methods. Concentration correction for molsidomine is necessary for samples after the second time point of each experiment, since a volume of 1.0 ml of the receiver fluid was removed and this volume was replaced with a fresh receiver fluid. The cumulative amount of molsidomine at each sampling point was calculated and plotted against the sampling time to give the skin permeation profile. The linear portion of the profile was used to estimate the steady state skin flux by linear regression analysis. Division of the slope of the regression line ($\mu$g/hr) by the permeation area (usually 0.689 cm$^2$) gives the steady state skin flux ($\mu$g/hr-cm$^2$). The acceptability of the skin flux was based on (1) the standard deviation of the experiments (usually triplicated), (2) visual examination of the permeation profiles, and (3) the standard deviations of each data point of all the replicated permeation profiles.

EXAMPLE 2

Primary Rabbit Skin Irritation Study

Primary rabbit skin irritation studies were conducted. The treatments included (1) four molsidomine matrix formulations, (2) a matrix formulation containing silicone 2920 and PGML, and (3) mineral oil as the control. The composition of the matrix formulations are described below.

Saturated Solubilities of Molsidomine

Since the solubilities of molsidomine in many solvents are known, we only determined solubilities of molsidomine in certain vehicles. Table III shows the solubilities in a number of solvent systems. It is soluble in propylene glycol and a solvent combination of propylene glycol with 10% of oleic acid, lauryl alcohol or PGML on the order of 90 mg/ml. In the phosphate buffers, 112 mg/ml was observed. Since the phosphate buffers were used as the receiver fluid, it was important to know if a sink condition could be maintained in each experiment. The solubilities of molsidomine in the phosphate buffer indicate that the receiver fluid can provide a sink condition for all the skin permeation experiments, since the final concentration of molsidomine in the receiver cell is generally less than 2-3 mg/ml.

TABLE III

| Solubilities of Molsidomine in Various Solvents | |
|---|---|
| Solvent Systems | Solubilities (mg/ml) |
| Propylene Glycol (PG) | 85.5 ± 3.9 |
| PG:Oleic Acid (10%) | 88.1 ± 0.7 |
| PG:Lauryl Alcohol (10%) | 89.3 ± 1.5 |
| PG:PGML (10%) | 92.9 ± 2.8 |
| Phosphate buffers | |
| pH 5.68 | 12.3 ± 1.8 |
| pH 6.80 | 12.1 ± 1.3 |

Skin Flux from Vehicle Formulations

Figure 2:
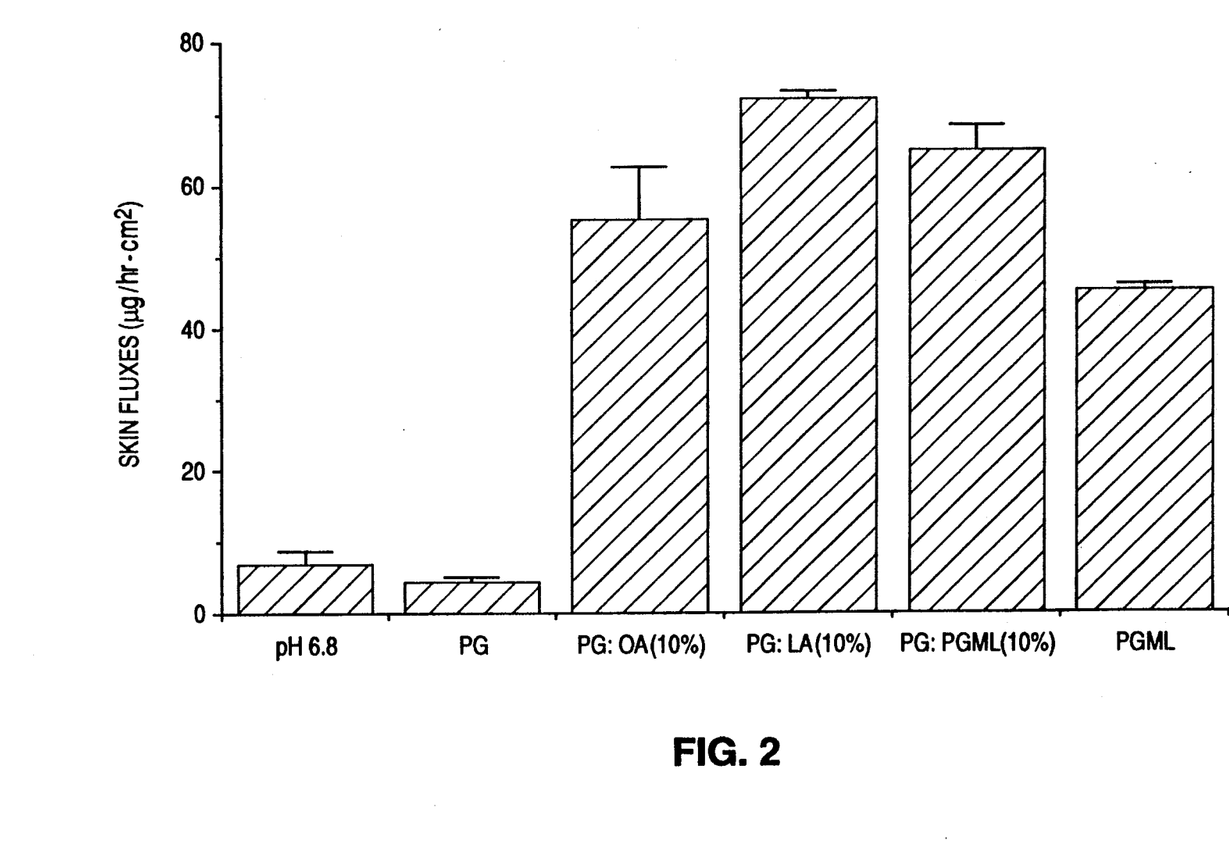
FIG. 2 is a graph showing the skin flux in six different vehicle formulations.

All the vehicle formulations were saturated with molsidomine; therefore, the thermodynamic activity of molsidomine in these formulations was expected to be maximal. FIG. 2 shows the skin flux of molsidomine from six vehicle formulations. Using propylene glycol alone, the skin flux was rather low; it was comparable to that obtained from a phosphate buffer solution. Very high skin fluxes, on the order of 50 to 75 $\mu$g/hr-cm$^2$, were obtained using PGML or a combination or propylene glycol with oleic acid, or lauryl alcohol, or PGML. These high skin fluxes were confirmed in a separate study by using epidermis with lower transepidermal water loss.

| PG:PGML (9:1) | 252.4 ± 47 $\mu$g/hr-cm$^2$ |
|---|---|
| PGML | 84.4 ± 2.3 $\mu$g/hr-cm$^2$ |

Since molsidomine is very stable in aqueous solutions of pH between 5 and 7, it is of interest to see if molsidomine can be delivered from aqueous solutions. A reasonable high skin flux of 9.7±1.9 $\mu$g/hr-cm$^2$ was obtained for pH 6.8. This suggests that a hydrophilic matrix such as hydrogel may be a useful reservoir for molsidomine.

In an independent study for matrix formulation made of silicone 2920 (80%), molsidomine (10%) and PGML (10%), using receiver fluids of pH 5.0 or 7.0 has no significant effect on the skin flux of molsidomine.

| pH | Flux ($\mu$g/hr-cm$^2$) |
|---|---|
| 5.0 | 10.6 ± 0.9 |
| 7.0 | 11.2 ± 0.7 |

Figure 3:
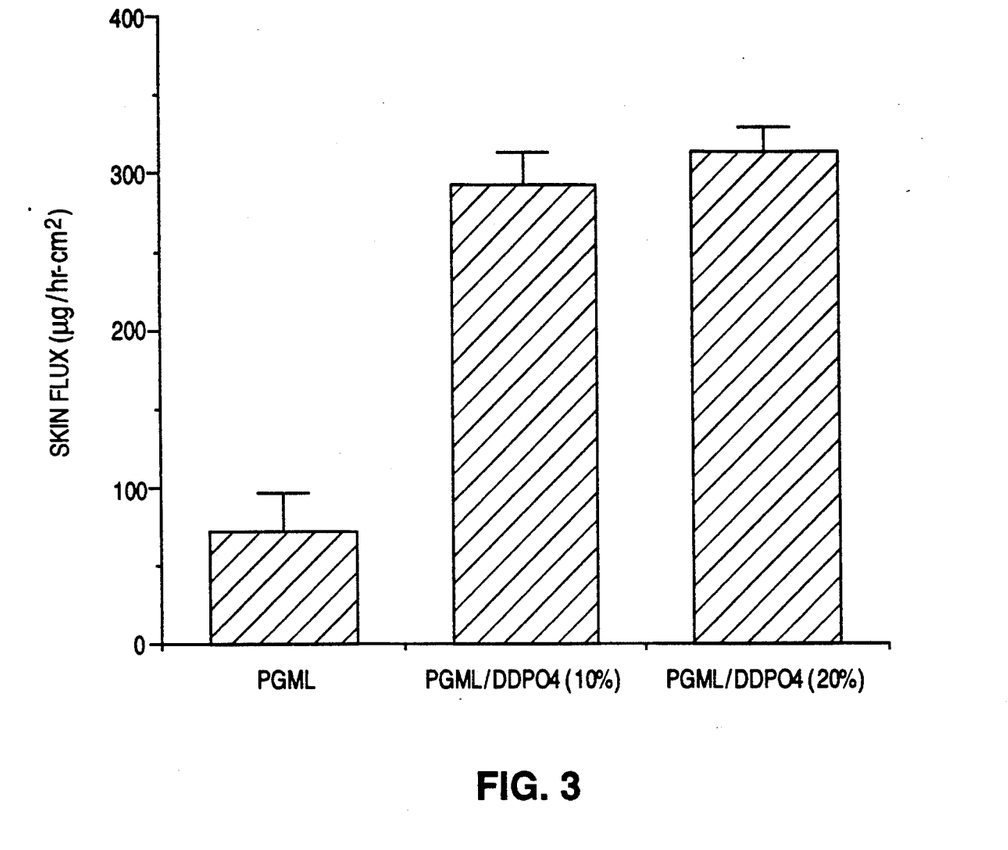
FIG. 3 is a graph showing the permeation enhancement obtained using different combinations of a monoalkyl phosphate as compared with a carrier not containing the monoalkyl phosphate.

A monoalkyl phosphate ester, mono-dodecyl phosphate (DDPO$_4$), which has very low human skin irritation potential, has been tested in the present investigation for skin flux enhancement. FIG. 3 shows the permeation enhancement of molsidomine. Addition of 10% DDPO$_4$ to PGML caused four times increment of skin flux. This absorption promoter also showed pirsidomine skin permeation enhancement.

Skin Flux from Monolithic Matrices

Figure 4:
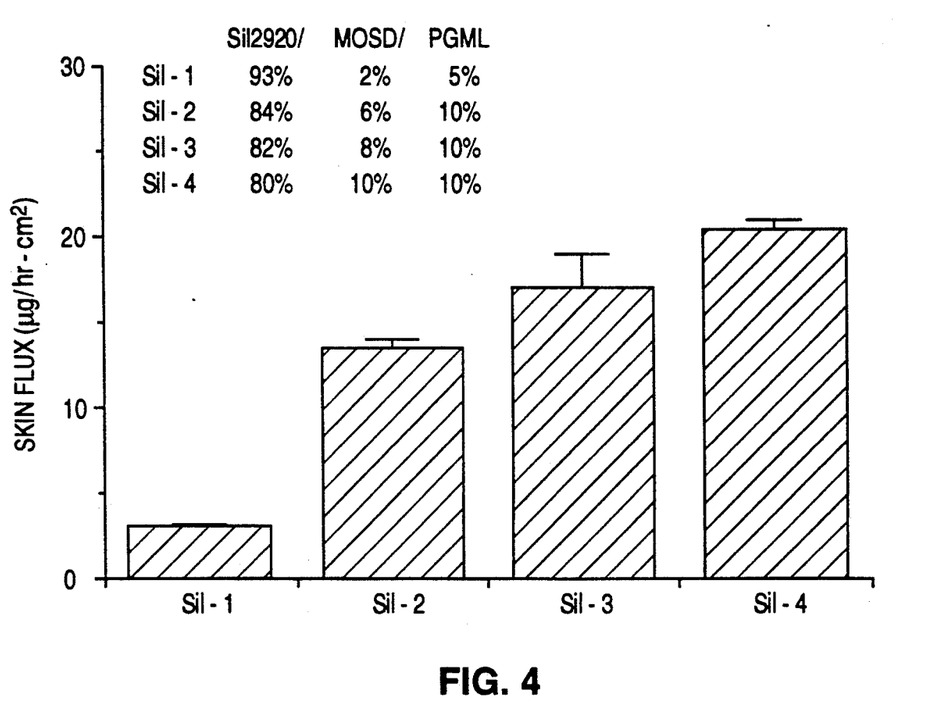
FIG. 4 is a graph showing the skin flux obtained for four different silicone matrices containing different amounts of molsidomine.

After having achieved high skin flux from solution formulations, matrix formulations were evaluated to determine whether good skin flux can be delivered. The four types of adhesives examined included Silicone 2920, Morstik 607, Gelva 788 and Gelva 2333. FIG. 4 shows the skin flux for four Silicone 2920 matrices loaded with various amounts of molsidomine and PGML. The skin flux appears to be molsidomine concentration dependent.

Figure 5:
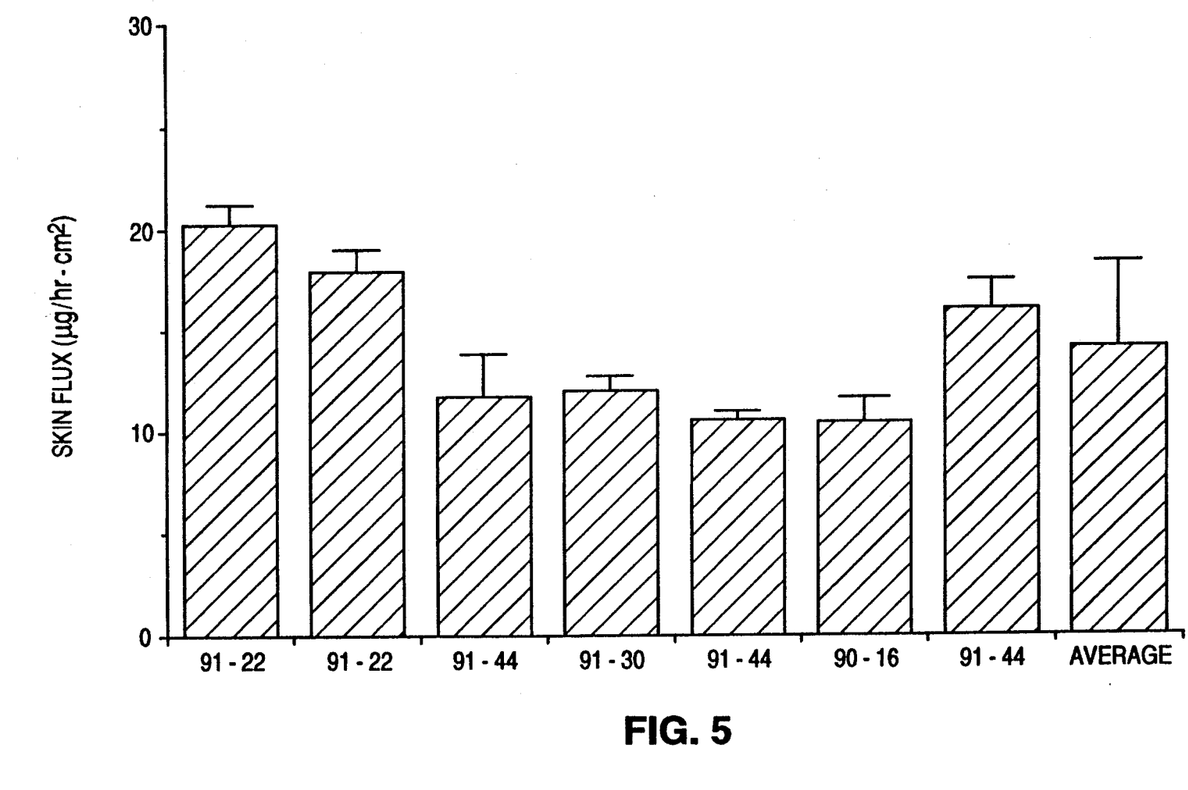
FIG. 5 is a graph showing the skin flux obtained with molsidomine using a variety of different skin samples for testing.

Since skin permeation variation is unavoidable, different donor skins were tested using a single silicone 2920 matrix formulation. FIG. 5 shows the molsidomine skin flux obtained from a variety of donor skins. The flux ranges from 11 to 20 $\mu$g/hr-cm$^2$ with an average of 14.3 $\mu$g/hr-cm$^2$. This information is helpful in evaluating the permeability of new donor skin for molsidomine.

Figure 6:
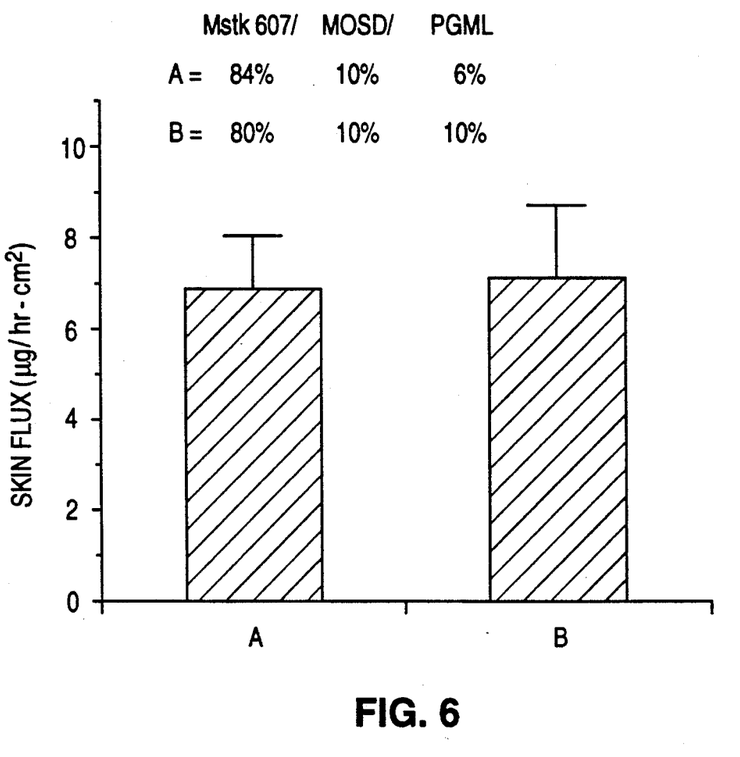
FIG. 6 is a graph showing the skin flux obtained with molsidomine formulations of the invention.
Figure 7:
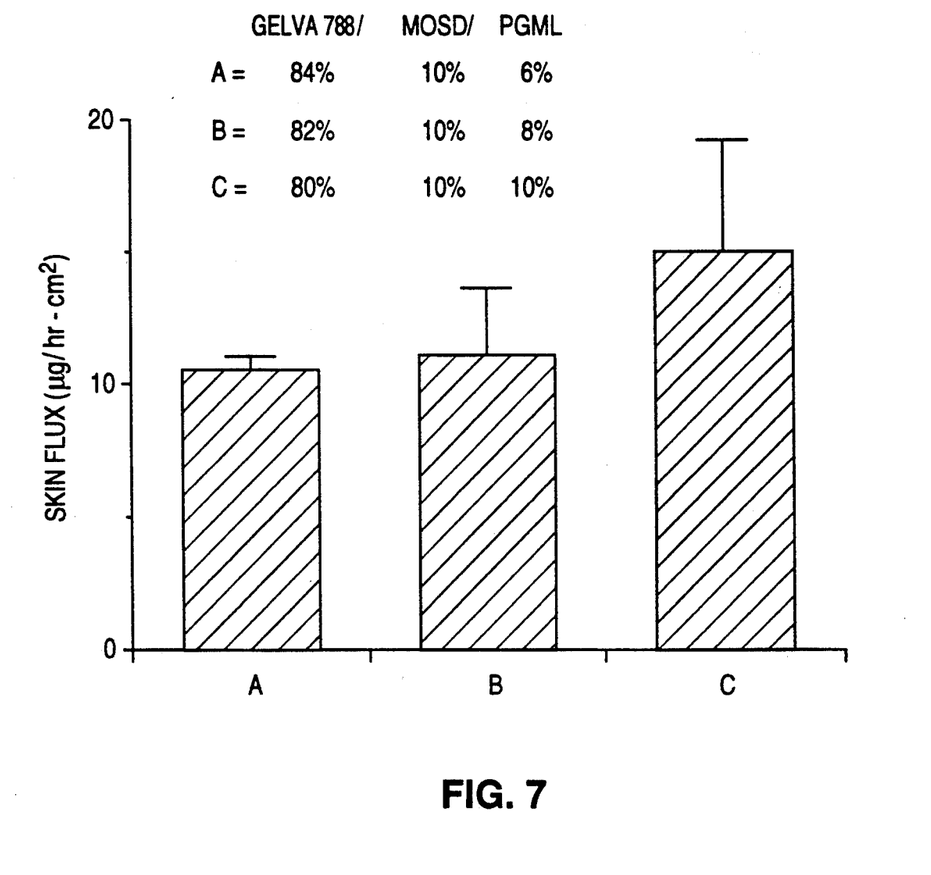
FIG. 7 is a graph showing the skin flux obtained with different molsidomine containing formulations of the invention.
Figure 8:
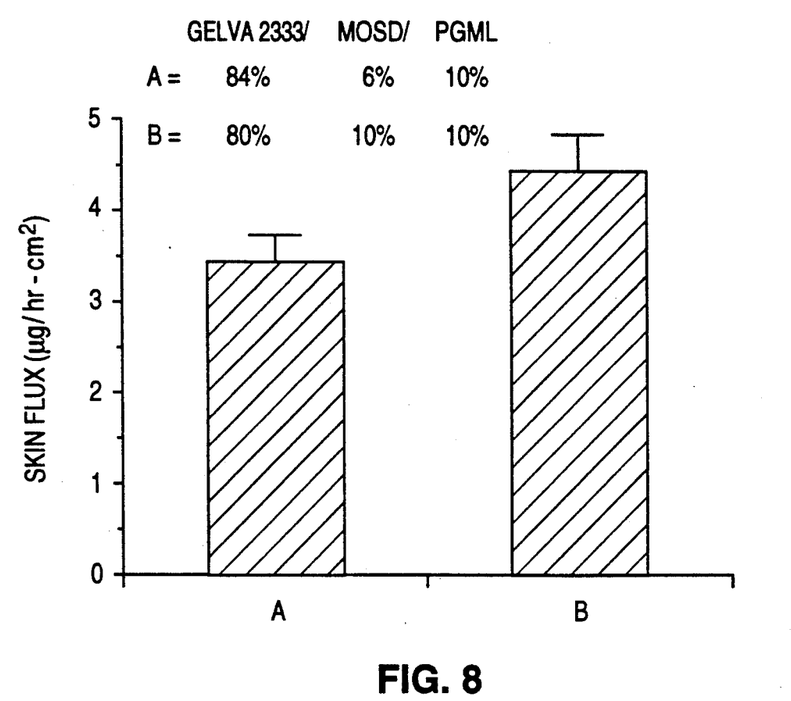
FIG. 8 is a graph showing the skin flux obtained for molsidomine containing formulations of the present invention.

Molsidomine can be delivered from Morstik 607 matrices at a flux of 7 $\mu$g/hr-cm$^2$ which meets with the target flux as shown in FIG. 6. The skin flux from Gelva 788 matrices is reasonably high as shown in FIG. 7, i.e., is in the range of 10 to 15 $\mu$g/hr-cm$^2$. The PGML concentration appears to have some effect on the flux. The skin flux from Gelva 2333 matrices is lower than the previous three types of matrices, ranging from 3.5 to 4.4 $\mu$g/hr-cm$^2$ as shown in FIG. 8.

Table IV shows a summary of skin flux for the best unoptimized matrix formulations evaluated.

TABLE IV

Molsidomine Monolithic Matrix Formulations

| Formulations | Skin Fluxes (µg/hr-cm$^2$) |
| --- | --- |
| Sil 2920/MOSD/PGML 80% 10% 10% | 14.3 ± 3.9 |
| Gelva 788/MOSD/PGML 80% 10% 10% | 15.0 ± 3.9 |
| Mstk 607/MOSD/PGML 80% 10% 10% | 7.2 ± 1.6 |
| Gelva 2333/MOSD/PGML 80% 10% 10% | 4.4 ± 0.4 |
| Target Skin Flux | 5.5 – 7.3 µg/hr-cm$^2$ |

Primary Rabbit Skin Irritation

The four best unoptimized matrix formulations were submitted for a primary rabbit skin irritation study. The calculated mean scores are shown in Table V. The formulations, together with the two controls (mineral oil and a matrix made of silicone 2920 and PGML alone), showed zero or very low skin irritation.

TABLE V

Primary Rabbit Skin Irritation Study on Monolithic Matrices

| Matrices | Mean Scores |
| --- | --- |
| Sil 2920/MOSD/PGML 80% 10% 10% | 0.28 |
| Gelva 788/MOSD/PGML 82% 10% 8% | 0.00 |
| Mstk 607/MOSD/PGML 80% 10% 10% | 0.17 |
| Gelva 2333/MOSD/PGML 80% 10% 10% | 0.00 |
| Sil 2920/PGML 90% 10% | 0.28 |
| Drakeol 21 (Mineral Oil) | 0.17 |

Rating:
0 0 - Non-irritating
0-1.9 - Mildly irritating
2-5.9 - Moderately irritating
6-8 - Severely irritating Based on the above-described experiments, it can be determined that molsidomine can be delivered through human cadaver epidermis in a wide range of skin fluxes up to 200 µg/hr-cm$^2$ from some vehicle solutions. Several promising monolithic matrices gave in vitro skin flux ranging from about 5 to 20 µg/hr-cm$^2$, which exceeded the target flux of 5.5-7.5 µg/hr-cm$^2$. A primary rabbit skin irritation study of several monolithic molsidomine matrices showed zero or very low skin irritation scores. Silicone 2920, Gelva 788 and Morstik 607 are potential polymeric materials for developing molsidomine transdermal therapeutic systems.

The instant invention is shown and described herein in what is considered to be the most practical, and preferred embodiments. It is recognized, however, that departures may be made therefrom which are within the scope of the invention, and that obvious modifications will occur to one skilled in the art upon reading this disclosure.

We claim:

1. A transdermal drug delivery device, comprising:
   a support base;
   a therapeutically effective amount of a pharmaceutically active drug thereon; and
   an absorption promoter in the form of a compound selected from the group consisting of monoalkyl phosphates containing 8 to 30 carbon atoms and pharmaceutically acceptable salts thereof.

2. The device of claim 1, wherein the pharmaceutically active drug is molsidomine.

3. The device of claim 1, further comprising:
   an additional absorption enhancer.

4. The device of claim 3, wherein the additional absorption enhancer is selected from the group consisting of a polyhydroxyl ester containing 8 to 30 carbon atoms, a fatty acid ester containing 8 to 30 carbon atoms, a polyhydroxyl alcohol containing 8 to 30 carbon atoms and a terpene containing 8 to 30 carbon atoms.

5. The device of claim 1, wherein the drug and absorption promoter are dispersed in a pharmaceutically acceptable carrier.

6. The device of claim 5, wherein the pharmaceutically acceptable carrier is in the form of a hydrogel.

7. A method of enhancing the transdermal permeation of a pharmaceutically acceptable drug, comprising the steps of:
   combining the pharmaceutically effective drug with an absorption promoter in the form of a monoalkyl phosphate containing 8 to 30 carbon atoms or pharmaceutically acceptable salt thereof to provide a formulation; and
   applying the formulation to the surface of a human.

8. The method of claim 7, wherein the surface is skin, the pharmaceutically active drug is molsidomine and the ratio of molsidomine to absorption enhancer is in the range of from 1:99% by weight to 15:85% by weight.

9. The method of claim 8, wherein the surface is a mucous membrane and the ratio of molsidomine to absorption enhancer is in the range of from 1:99% by weight to 15:85% by weight.

10. The method of claim 7, wherein the formulation is further comprised of an additional absorption enhancer selected from the group consisting of a polyhydroxyl ester containing 8 to 30 carbon atoms, a fatty acid ester containing 8 to 30 carbon atoms, a polyhydroxyl alcohol containing 8 to 30 carbon atoms and a terpene containing 8 to 30 carbon atoms.

11. The method of claim 10, wherein the monoalkyl phosphate or salt thereof contains 12 carbon atoms.

12. A pharmaceutical formulation, comprising:
   a therapeutically effective amount of molsidomine; and
   an absorption enhancer comprising mono-dodecyl phosphate and propylene glycol monolaurate.

13. The formulation of claim 12 wherein the ratio of molsidomine to absorption enhancer is in the range of from 1:99% by weight to 15:85% by weight.

14. A transdermal drug delivery device, comprising:
   a support base;
   a therapeutically effective amount of molsidomine; and
   an absorption promoter in the form of a compound selected from the group consisting of monoalkyl phosphates containing 8 to 30 carbon atoms and pharmaceutically acceptable salts thereof.

* * * * *